United States Patent
Jee et al.

(10) Patent No.: US 8,186,060 B2
(45) Date of Patent: May 29, 2012

(54) METHOD TO PROVIDE INITIAL TENSION FOR COIL SPRING AND ITS APPLICATION

(75) Inventors: Kwang-Koo Jee, Seoul (KR); Yoon-Bae Kim, Seoul (KR); Jun-Hyun Han, Seoul (KR)

(73) Assignee: Korea Institute of Science and Technology (KR)

( * ) Notice: Subject to any disclaimer, the term of this patent is extended or adjusted under 35 U.S.C. 154(b) by 1315 days.

(21) Appl. No.: 11/843,035

(22) Filed: Aug. 22, 2007

(65) Prior Publication Data

US 2008/0047144 A1    Feb. 28, 2008

(30) Foreign Application Priority Data

Aug. 24, 2006  (KR) .................. 10-2006-0080747
May 4, 2007    (KR) .................. 10-2007-0043721

(51) Int. Cl.
*B21F 35/00*    (2006.01)

(52) U.S. Cl. .............. 29/896.93; 29/896.9; 29/896.91; 29/896.92

(58) Field of Classification Search ..... 29/896.9–896.93
See application file for complete search history.

(56) References Cited

U.S. PATENT DOCUMENTS 4,719,683 A * 1/1988 Ulbing .................. 29/896.9

FOREIGN PATENT DOCUMENTS

| JP | 59-179767 | 10/1984 |
|----|-----------|---------|
| JP | 64-046039 | 2/1989 |
| JP | 02-117731 | 5/1990 |
| JP | 3-13553 | 1/1991 |
| JP | 03-13553 | 1/1991 |
| JP | 03-066957 | 3/1991 |
| JP | 03-177550 | 8/1991 |
| JP | 05-212065 | 8/1993 |
| JP | 5-212065 | 8/1993 |
| JP | 07-31433 | 12/1995 |

OTHER PUBLICATIONS

Korean Office Action dated Jul. 11, 2008.
Office Action issued by Japanese Patent Office and mailed on Jul. 5, 2011 in connection with corresponding Japanese application No. 2009-525484.
Chinese Office Action dated Apr. 28, 2010.

* cited by examiner

*Primary Examiner* — Richard Chang
(74) *Attorney, Agent, or Firm* — Ostrolenk Faber LLP (57) ABSTRACT

A method for enhancing an initial tension by changing a wound direction of a coil spring. A large and precise initial tension is provided to the coil spring. An actuator having an excellent function is prepared by using a shape memory alloy. Each shape of the coil spring at high and low temperatures can be controlled by a flexible shape memory effect.

2 Claims, 13 Drawing Sheets

METHOD TO PROVIDE INITIAL TENSION FOR COIL SPRING AND ITS APPLICATION

TECHNICAL FIELD

The present invention relates to a coil spring, and more particularly, to a method for precisely providing a large initial tension to a coil spring.

BACKGROUND ART

Figure 1:
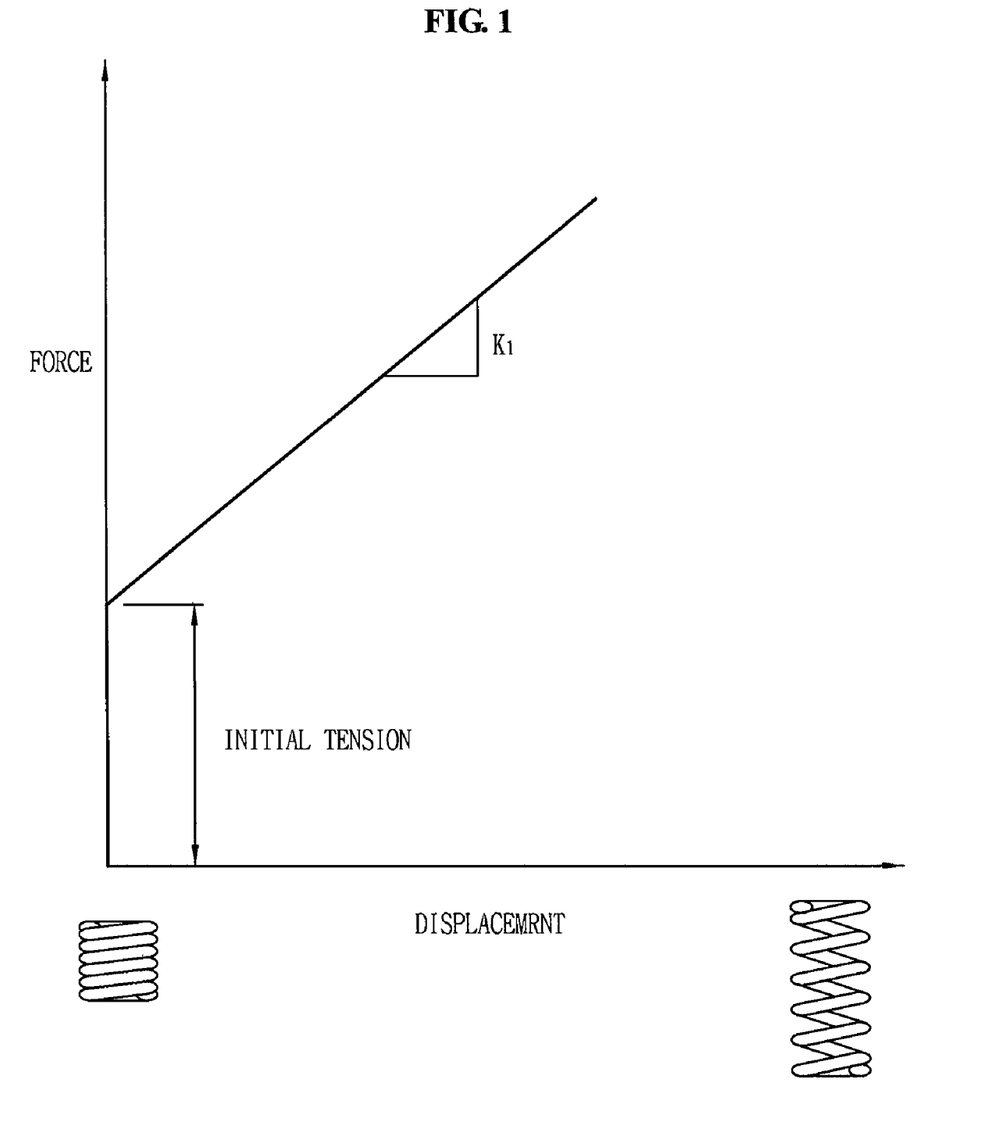
FIG. 1 is a conceptual view of an initial tension.

An initial tension is a force of a tension spring to be contracted before being deformed by an external force. As shown in FIG. 1, the tension spring starts to be deformed when a force corresponding to its initial tension is applied thereto. A length of the tension spring can be shortened by using the initial tension, so that a space can be effectively utilized and a size of a component can be minimized.

In order for the tension spring to have an initial tension, a coil spring has to be wound by a minus pitch.

However, the minus pitch has the following problems.

Since the minus pitch is invisible, it is difficult to implement a precise value and a large value.

Furthermore, in the conventional method using a remaining stress, the stress is released when the coil spring is wound in a heating process, or when the coil spring is thermally processed after being wound in a cooling process. Accordingly, it is very difficult to provide an initial tension to the coil spring.

DISCLOSURE OF THE INVENTION

Therefore, it is an object of the present invention to provide a method for providing a large and precise initial tension to a coil spring.

To achieve these objects, there is provided a method for providing a large and precise initial tension to a coil spring, comprising: preparing an opened coil spring having a predetermined gap between coils when an external force is not applied thereto by winding the coils clockwise or counterclockwise; and preparing a closed coil spring that maintains a closed shape in a reverse direction when an external force is not applied thereto.

According to another aspect of the present invention, there is provided a method for restoring a permanently deformed coil spring into an original state, comprising: preparing a permanently deformed coil spring by excessively tensioning a closed coil spring wound clockwise or counterclockwise; obtaining a closed coil spring in a reverse direction by reversely changing the wound direction of the coil spring and by adhering coils to each other; and obtaining the initial closed coil spring by excessively tensioning the closed coil spring in a reverse direction, by reversely re-changing the wound direction of the coil spring, and by adhering coils to each other.

According to still another aspect of the present invention, there is provided a coil spring provided with an initial tension manufactured by the method for providing a large and precise initial tension to a coil spring, wherein the coil spring has a contraction force therein under a state that an external force is not applied thereto.

According to yet still another aspect of the present invention, there is provided a linear actuator comprising: a coil spring formed of a shape memory alloy; and a bias spring for providing a deformation force opposite to a deformation force of the coil spring, wherein the coil spring is a tension spring manufactured by the method for providing a large and precise initial tension to a coil spring and having a contraction force therein under a state that an external force is not applied thereto.

MODES FOR CARRYING OUT THE PREFERRED EMBODIMENTS

Reference will now be made in detail to the preferred embodiments of the present invention, examples of which are illustrated in the accompanying drawings.

A method for providing an initial tension to a coil spring will be explained with reference to FIGS. 2A and 2B.

Figure 2A:
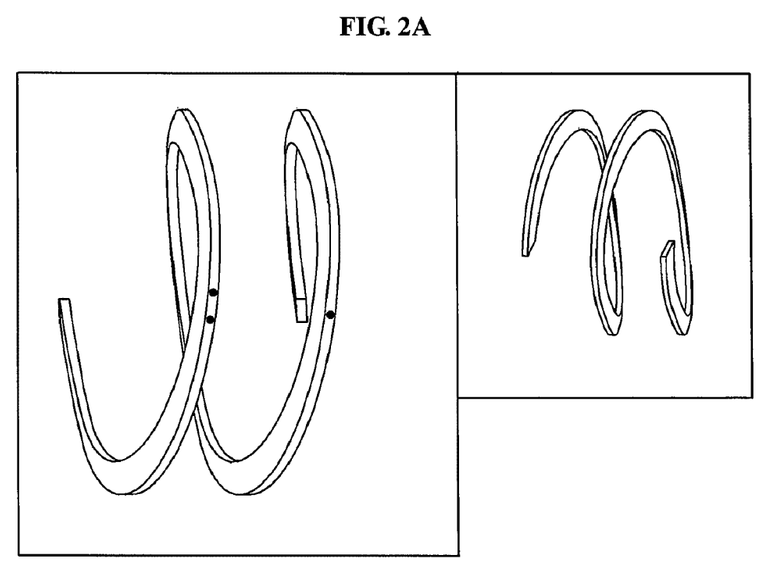
FIGS. 2A and 2B show photos representing a principle to provide an initial tension to a coil spring according to the present invention.
Figure 2B:
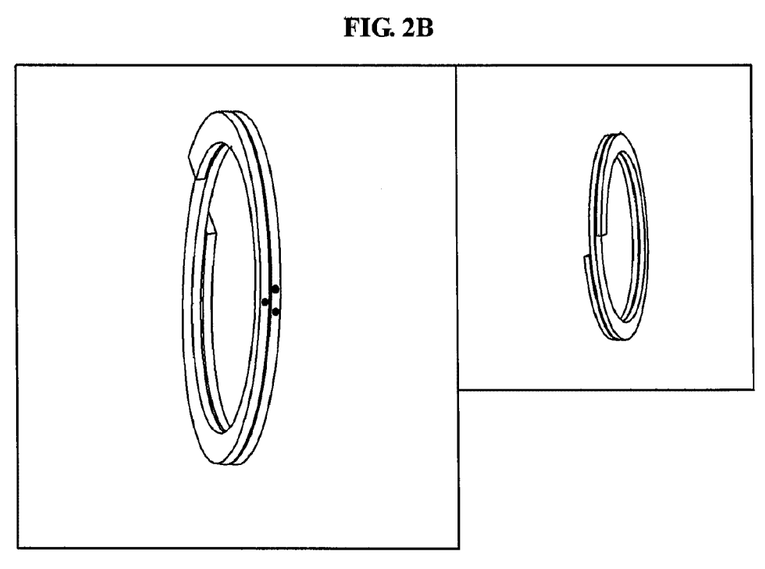

Referring to FIG. 2A, an opened coil spring has an expansion force. When a position of a coil of the coil spring is changed, the coil spring becomes a closed coil spring as shown in FIG. 2B. Herein, the expansion force of the coil spring is changed into a compression force which is an initial tension. Changing the position of the coil means that a wound direction of the coil spring is changed. The coil spring is wound counterclockwise in FIG. 2A, whereas it is wound clockwise in FIG. 2B. Small photos are captured in another angle so as to clarify the wound direction of the coil spring.

In the present invention, an opened coil spring wound clockwise or counterclockwise is re-wound in a reverse direction thus to prepare a closed coil spring (tension spring), and an initial tension is provided to the coil spring.

A method for changing a wound direction of the opened coil spring will be explained in more detail with reference to FIGS. 3A to 3D.

Figure 3A:
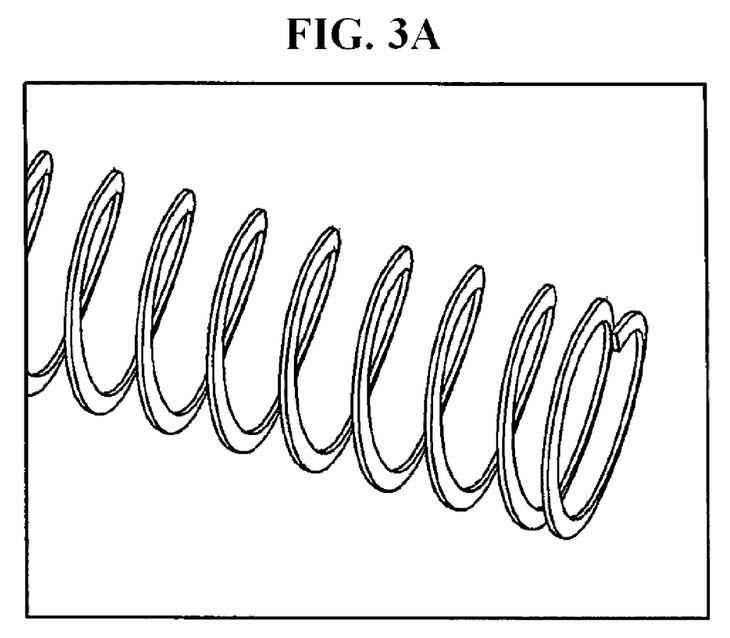
FIGS. 3A to 3D show photos representing a method for providing an initial tension to a coil spring according to the present invention, in which a wound direction of the coil spring is changed.
Figure 3B:
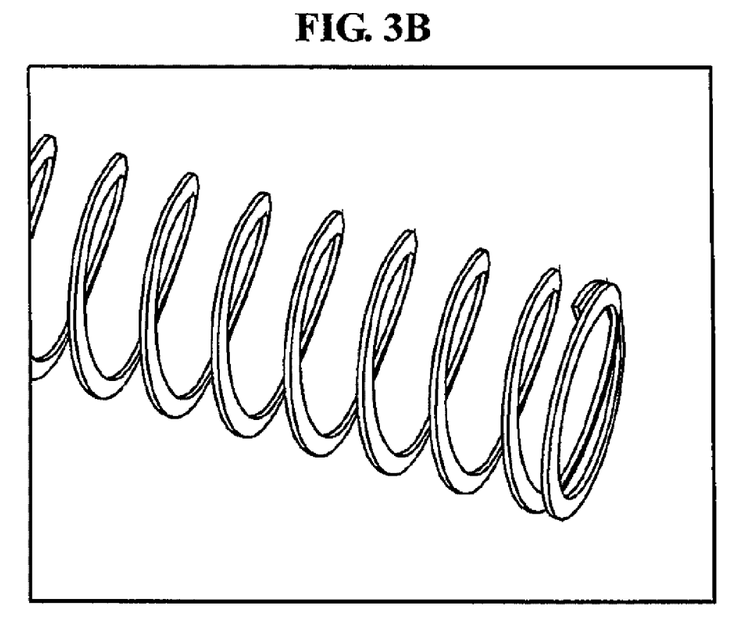
Figure 3C:
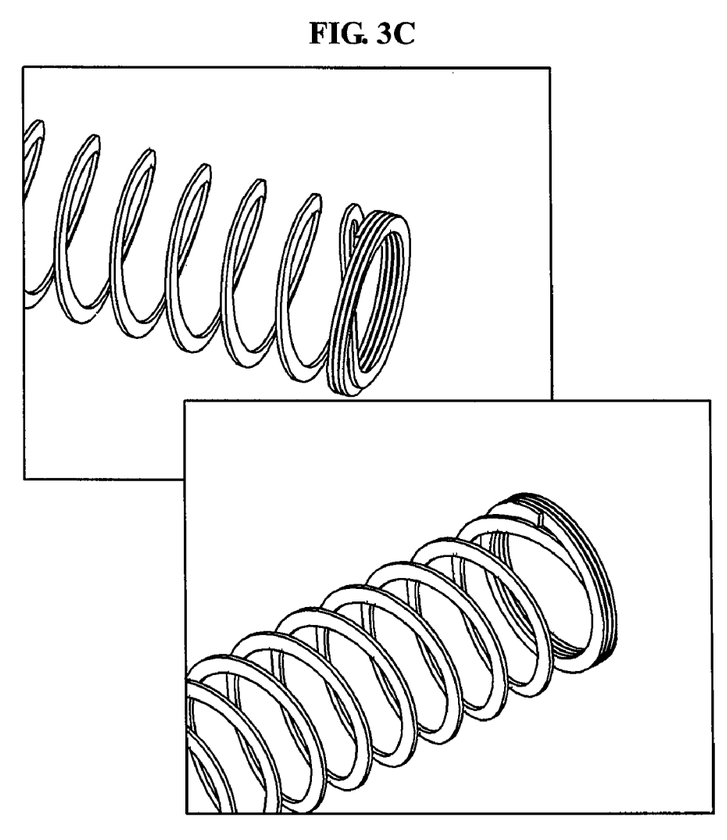
Figure 3D:
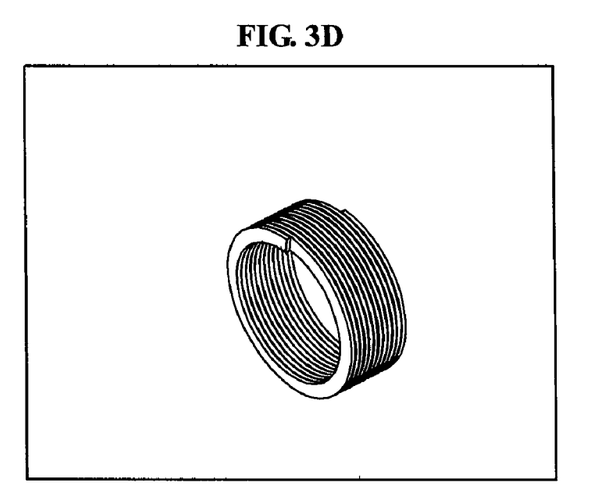

First, a coil spring is depicted that maintains a non-adhered state of coils having a predetermined gap (i.e., an opened state) when an external force is not applied to the coils wound clockwise. In the preferred embodiment, a coil spring having coils wound clockwise is prepared. However, a coil spring having coils wound counterclockwise may be prepared (refer to FIG. 3A). Then, a right end of the coil spring is disposed on the left first coil (refer to FIG. 3B). Then, the first coil (the rightmost coil) is pulled out in a right direction. Accordingly, the first coil is adhered to a right side of the right end counterclockwise. Then, a second coil connected to the first coil is pulled out in a right direction thus to be adhered to a right side of the first coil counterclockwise. Then, a third coil connected to the second coil is pulled out in a right direction thus to be adhered to a right side of the second coil counterclockwise (refer to FIG. 3C). FIG. 3C shows two photos captured in different angles. When the above process is repeated, the wound direction of the coil spring is changed into a reverse direction thus to change the opened state of the coil spring into a closed state as shown in FIG. 3D. That is, the right end of the opened coil spring wound clockwise is positioned at a left end of the closed coil spring wound counterclockwise after the process.

In the preferred embodiment, the right end of the opened coil spring is moved to the left side. However, it is also possible to move the left end of the opened coil spring to the right side.

Referring to FIGS. 4A to 4D, the wound direction of the opened coil spring can be changed into a reverse direction by using a supplementary device of an outer diameter having a similar size to an inner diameter of the opened coil spring.

Figure 4A:
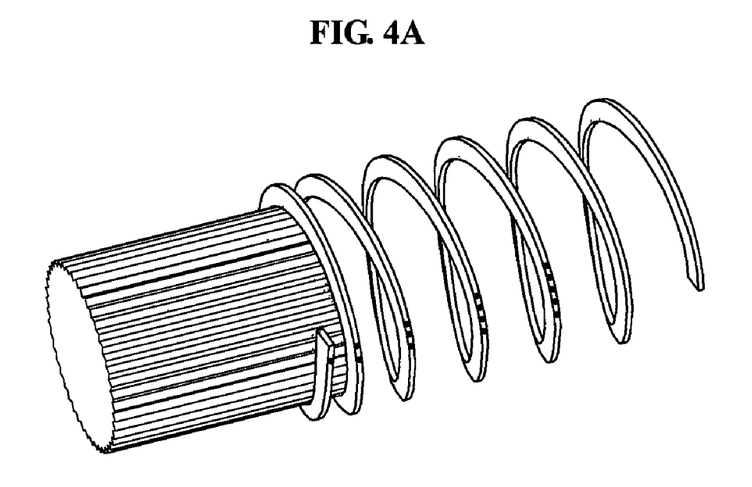
FIGS. 4A to 4D show photos representing a process for facilitating to change a wound direction of the coil spring by using a supplementary device.
Figure 4B:
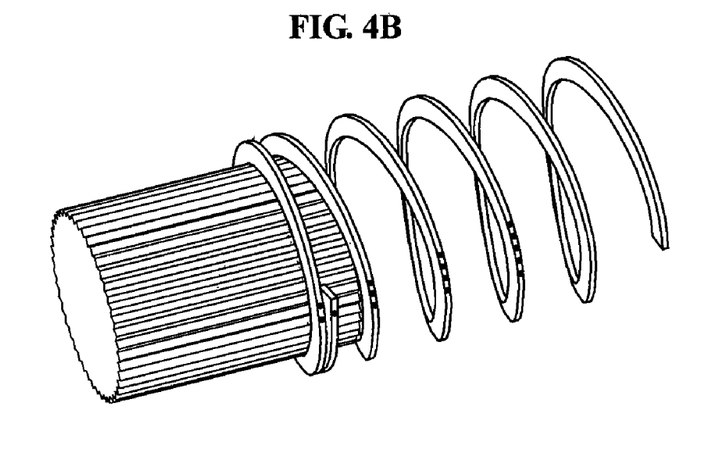
Figure 4C:
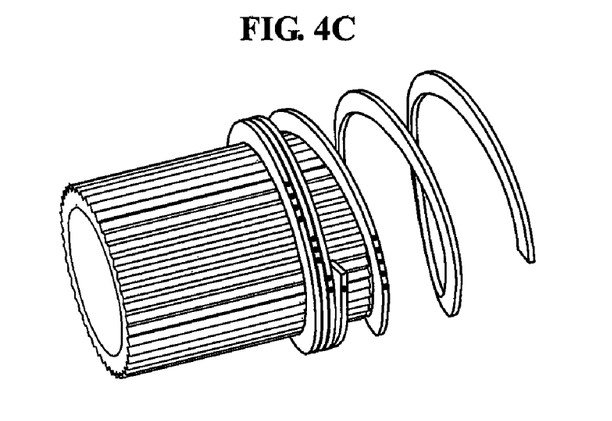
Figure 4D:
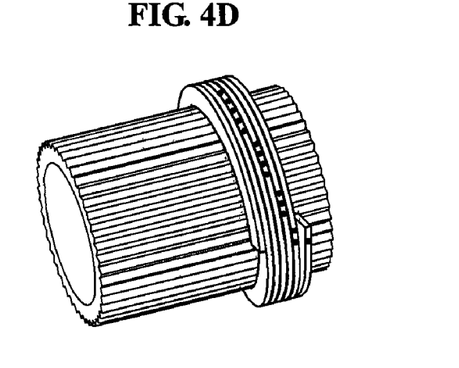

More concretely, the supplementary device of FIG. 4A is inserted into the left end of the opened coil spring and the first coil connected thereto. Then, the left end of the opened coil spring is positioned between the first coil and a second coil, and the position of the left end is exchanged with the position of the first coil (refer to FIG. 4B). Then, one set of the left end and the first coil is positioned between the second coil and a third coil, and the position of the one set is exchanged with the position of the second coil. As the above process is repeated, the wound direction of the opened coil spring is changed into a reverse direction and a closed coil spring is prepared (refer to FIGS. 4C and 4D).

Figure 5A:
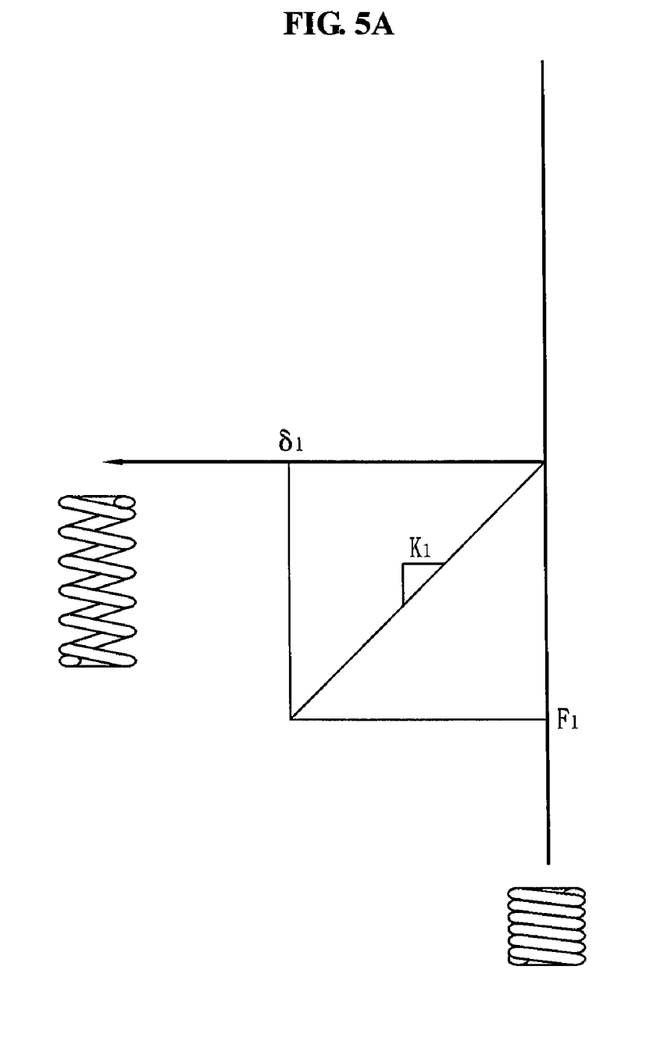
FIGS. 5A to 5C are views schematically showing a principle to provide an initial tension to a coil spring according to the present invention.
Figure 5B:
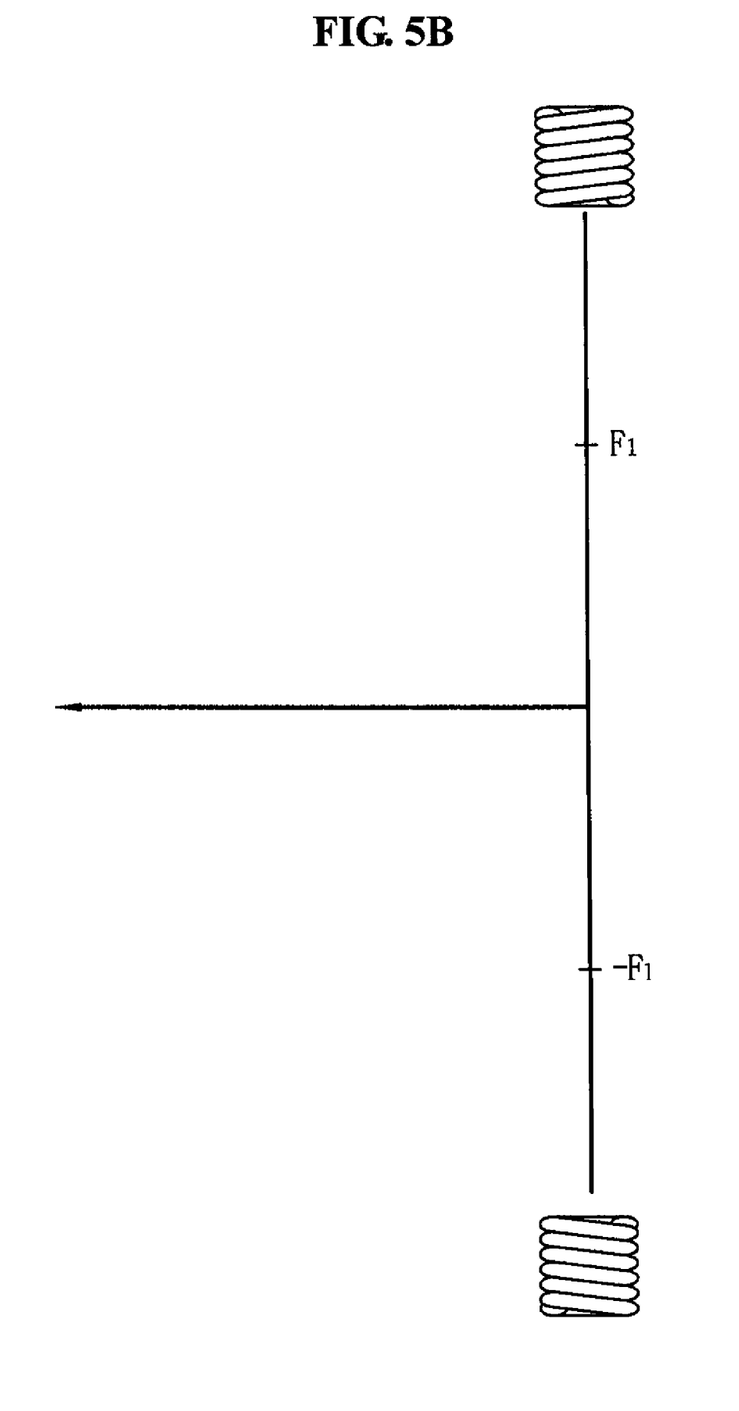
Figure 5C:
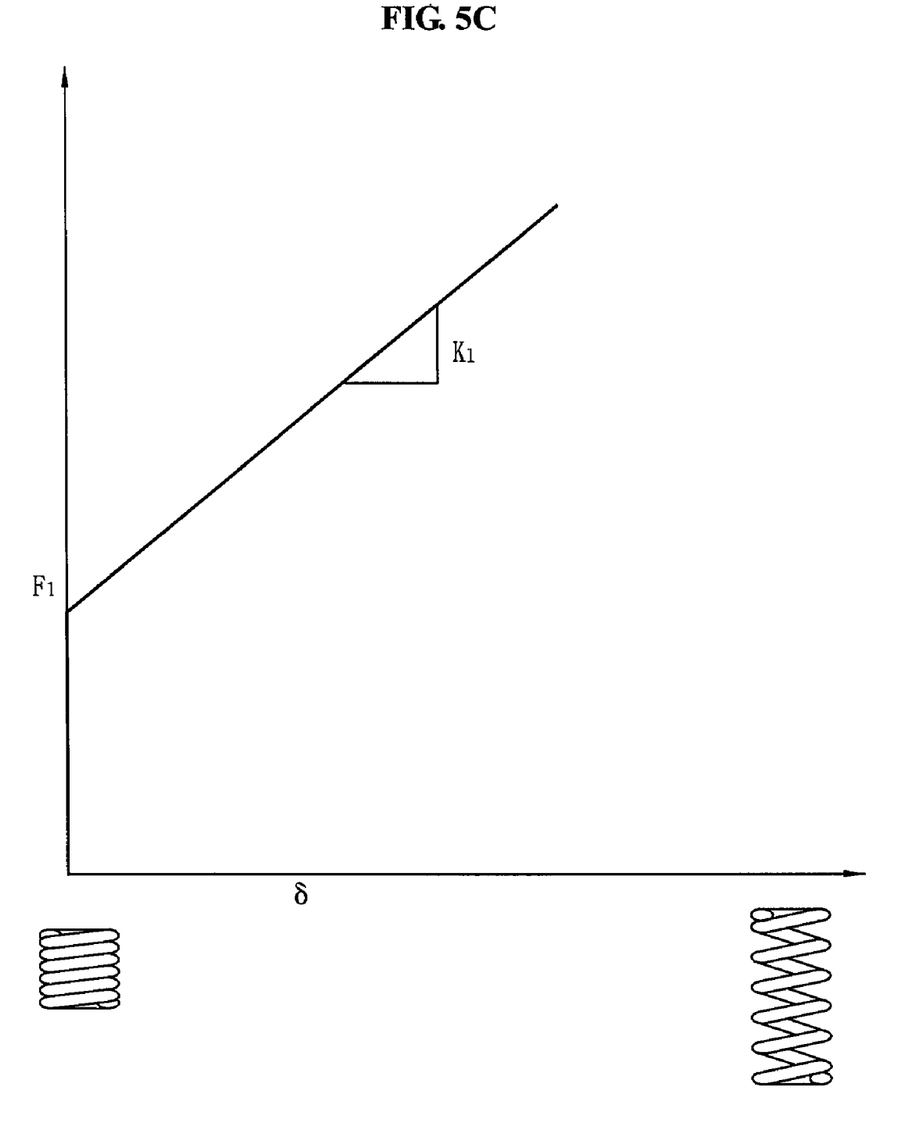

A method for providing an initial tension to a coil spring according to the present invention will be explained with reference to FIGS. 5A to 5C.

It is assumed that a coil spring opened by a displacement of $\delta_1$ (wound counterclockwise) has a spring constant of $K_1$. In order to deform the coil spring by a compression, a compression force of $-F1$ is required (refer to FIG. 5A). When the wound direction of the coil spring is changed into a reverse (counterclockwise) direction, an opposite force, F1 to the $-F1$ is applied. The coil spring is in a state to be contracted with the F1 (Refer to FIG. 5B). That is, the closed coil spring has a contract force corresponding to the F1 before an external stress is applied thereto. Herein, the contract force means an initial tension. When the coil spring having the initial tension of F1 is deformed, a behavior of FIG. 5C is shown. That is, the coil spring initially has an infinite spring constant, but has a finite value after an initial tension. Since the initial tension is obtained by multiplying k1 and $\delta_1$ to each other (F1=k1×$\delta_1$), a precise initial tension can be provided by controlling the k1 and $\delta_1$.

Preferred Embodiment 1

A tension coil spring having the number of effective windings of 10 and having a spring constant of 2N/mm was prepared. Herein, it is assumed that a compression spring and a tension spring has the same spring constant in a small displacement. In order to obtain an initial tension of 50N, an opened coil spring having a displacement ($\delta_1$) of 25 mm was prepared. As the wound direction of the opened coil spring is changed, a closed coil spring having an initial tension of 50N was obtained.

As a result, the initial tension was more increased than that of the conventional art by more than five times, and was precisely controlled. Furthermore, since the wound direction of the coil spring is changed, the coil spring can be easily applied even in a thermal process.

Preferred Embodiment 2

When a technique for enhancing an initial tension by changing a wound direction of a coil spring is applied to a coil spring formed of a shape memory alloy (SMA), the following advantages are obtained.

Since the SMA is finally thermal-processed so as to memorize a shape, it is difficult to provide an initial tension to the coil spring by the conventional method.

A coil spring having a diameter of 22.0 mm and the number of effective windings of 10 was prepared by using coils having a composition of 50.5Ni—Ti, a thickness of 0.75 mm, and a width of 2.0 mm. A comparison object was a closed coil spring (sample 'A'), and the coil spring of the present invention (sample 'B') was wound so that a distance between coils can be 12 mm. The samples 'A' and 'B' were thermally-processed for 30 minutes at a temperature of 800° C., thereby performing a shape memory process. The wound direction of the sample 'B' was reversely changed, thereby implementing a closed coil spring.

Figure 6:
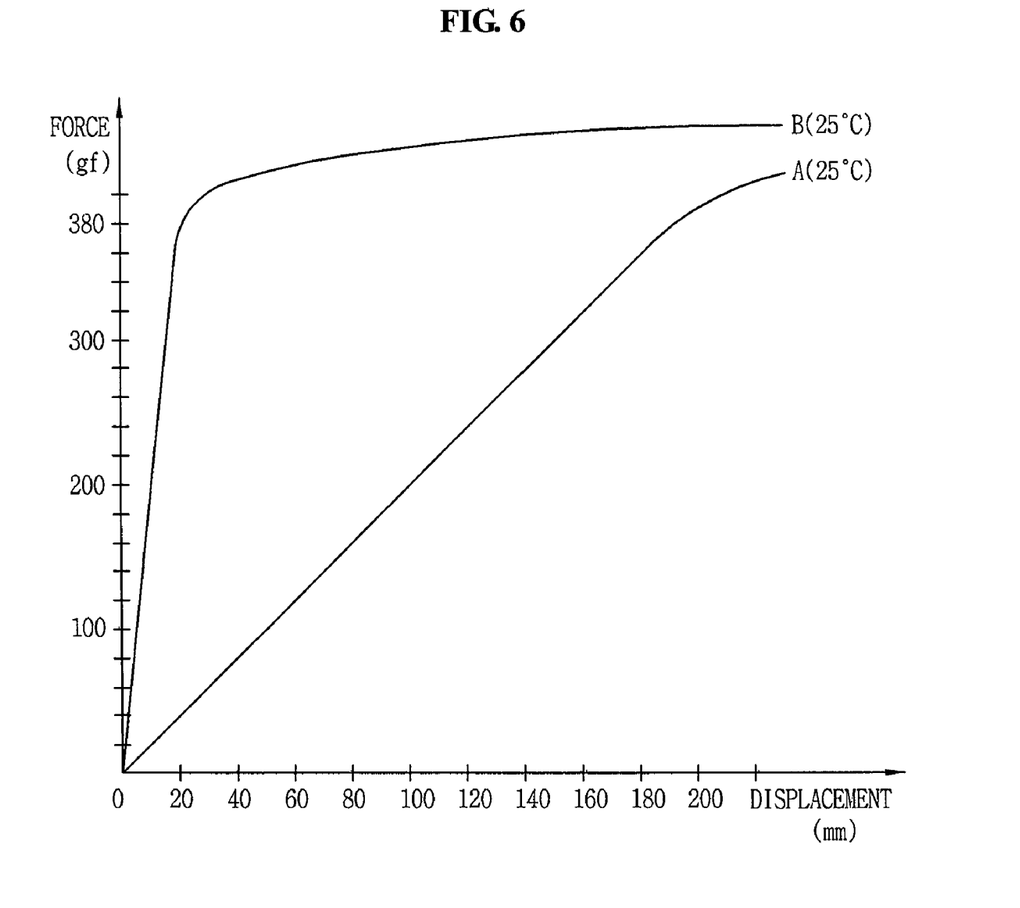
FIG. 6 shows curves representing tensions of samples 'A' and 'B' measured at a temperature of 25° C.

The SMA having the composition of 50.5Ni—Ti has a high temperature phase at a temperature of 25° C. Referring to FIG. 6, the sample 'B' has a spring constant larger than that of the sample 'A' at a temperature of 25° C. The sample 'B' of the present invention has a spring constant of 19 gf/mm, whereas the sample of 'A' has a spring constant of 2 gf/mm. The spring constant originally shown as an infinite value was shown as a finite value since the SMA has been deformed with a predetermined speed. In the preferred embodiment, the coil spring formed of an SMA was applied. However, a coil spring formed of a general metal may be also applied to the present invention so as to increase a spring constant by changing a wound direction of coils.

Figure 7:
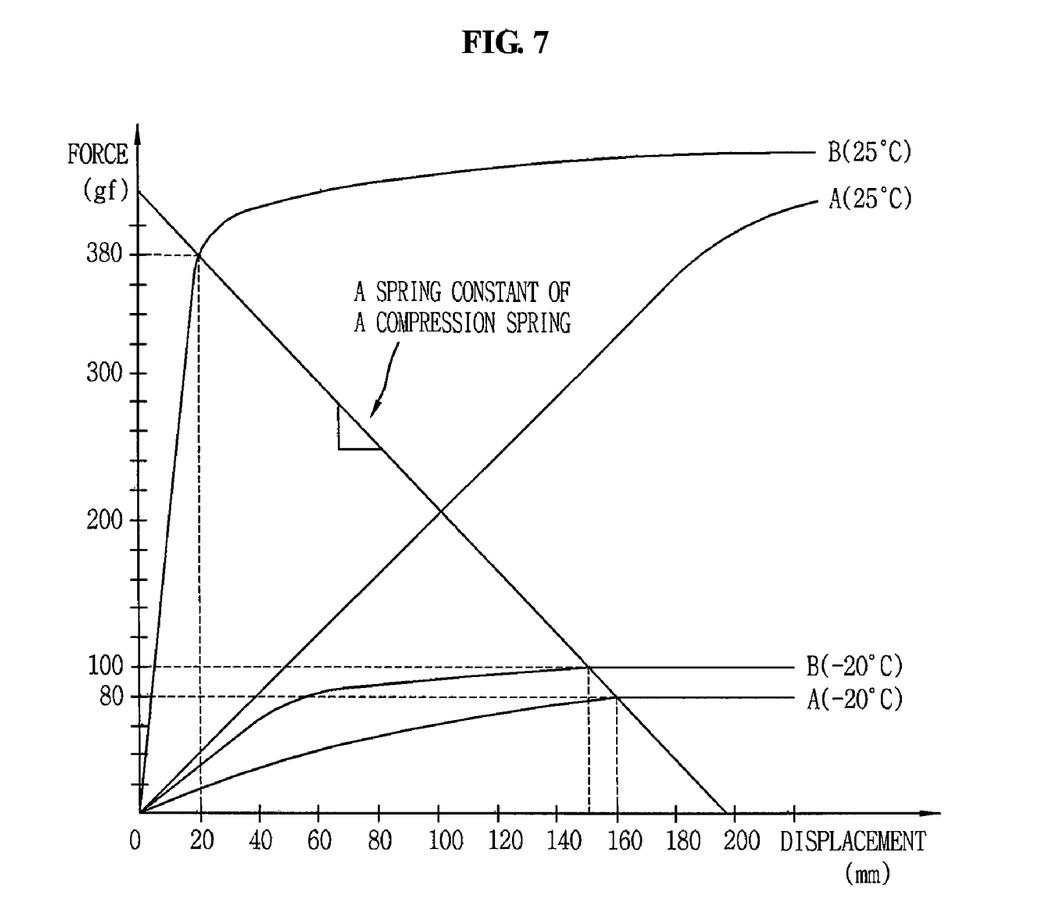
FIG. 7 is a graph showing each displacement of samples 'A' and 'B' according to a temperature.

FIG. 7 shows each tension curve of the samples 'A' and 'B' measured at temperatures of 25° C. and −20° C. The sample of 'A' has a high temperature phase, and the sample of 'B' has a low temperature phase. A spring constant at a high temperature is increased as shown in FIG. 6. At a temperature of −20° C., the sample 'B' has a spring constant larger than that of the sample 'A', but has a similar yield strength to that of the sample 'A'.

A compression spring formed of a general metal (having an elastic coefficient of 2 gf/mm and a displacement of 200 mm) was installed in the coil spring formed of an SMA. The compression spring is linearly deformed according to a deformation amount without depending on a temperature, which is shown in FIG. 7. Accordingly, a displacement of the SMA coil spring is determined according to a temperature at a point where a compression force of the SMA coil spring is equal to an expansion force of the compression spring.

A displacement of the SMA coil spring having the compression spring therein was measured at temperatures of 25° C. and −25° C. The displacement of the sample of 'A' was 95 mm at a temperature of 25° C. and was 160 mm at a temperature of −20° C., and a moving distance was approximately 65 mm. However, the displacement of the sample of 'B' was 18 mm at a temperature of 25° C. and was 145 mm at a temperature of −20° C., and a moving distance was approximately 127 mm corresponding to approximately two times of the moving distance of the sample 'A'.

The SMA uses an elastic deformation at a high temperature and a plastic deformation at a low temperature. Accordingly, even when a spring constant is increased, a yield strength is not greatly changed. Accordingly, a position of the coil spring is scarcely changed at a low temperature, whereas a position thereof is greatly changed at a high temperature. As a result, a moving distance of the coil spring can be greatly increased. By increasing the moving distance of the coil spring, an actuator having an excellent function can be prepared.

Preferred Embodiment 3

In the present invention, a permanently deformed coil spring can be restored to the original shape.

Figure 8A:
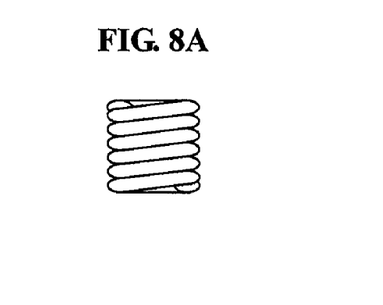
FIGS. 8A to 8E are schematic views showing a principle to restore a coil spring having undergone a permanent deformation into an original state.
Figure 8B:
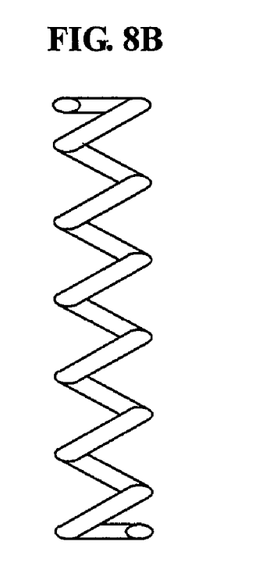
Figure 8C:
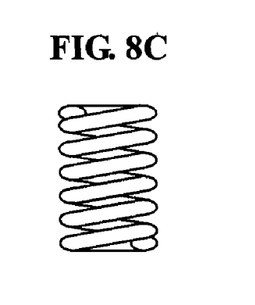

When a closed tension spring wound clockwise (refer to FIG. 8A) is excessively deformed (refer to FIG. 8B), the tension spring is permanently deformed (refer to FIG. 8C). In order to implement the original closed tension spring, a compression has to be excessively performed. However, the tension spring was not restored to the original shape by the conventional method.

Figure 8D:
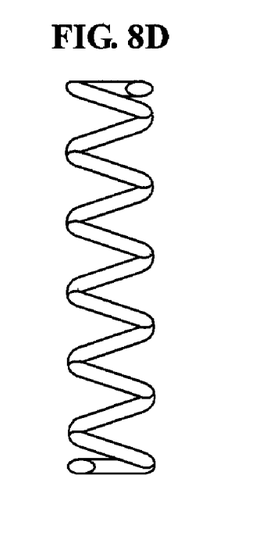
Figure 8E:
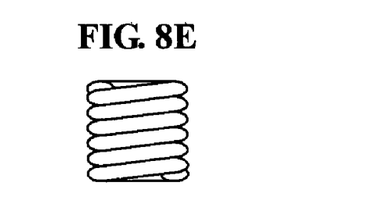

Accordingly, the wound direction of the permanently deformed coil spring (refer to FIG. 8C) is changed into a counterclockwise direction. Then, the coil spring was excessively tensioned (refer to FIG. 8D), which corresponds to excessively compressing the coil spring wound in a clockwise direction. The wound direction of the coil spring having been properly tensioned is re-changed into a clockwise direction, thereby obtaining the original closed coil spring shown in FIG. 8A or FIG. 8E.

Preferred Embodiment 4

An experiment for a flexible shape memory effect of the SMA was performed.

Figure 9A:
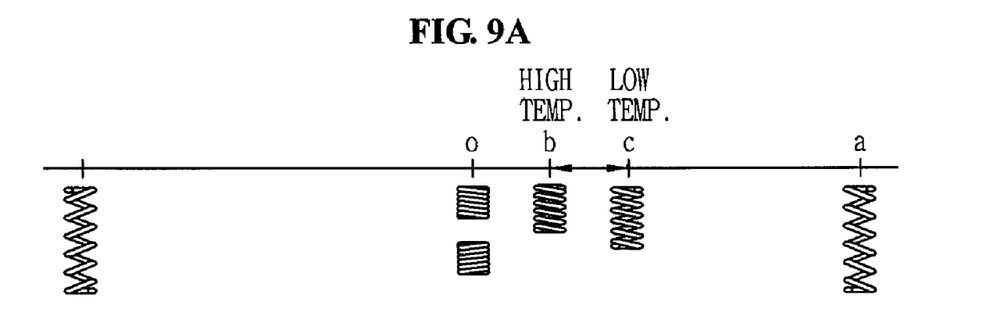
FIGS. 9A to 9E are graphs showing a method for controlling a shape of a coil spring having a flexible shape memory effect.

The flexible shape memory effect is a phenomenon that a shape of an object is flexibly changed when a heating process and a cooling process are repeated. The flexible shape memory effect may be implemented by generating an electric potential or a precipitate. FIG. 9A shows a flexible shape memory effect by a potential. A closed coil spring (o) is greatly tensioned (a), and then is heated thus not to restore into the original shape (o) but to deform by (b). Then, the coil spring is cooled thus to become (c). As a heating process and a cooling process are repeated, the coil spring has each shape of (b) and (c), which is called as a flexible shape memory effect. The flexible shape memory effect is implemented by a potential applied during a deformation, which causes a deformation amount that can not be recovered. Accordingly, in the conventional art, it was impossible to obtain a completely closed shape with implementing the flexible shape memory effect. It is advantageous to widen the coil spring in a closed state than in an opened state. The shape of the coil spring having the flexible shape memory effect at high and low temperatures is not controlled by the conventional art. However, the shape of the coil spring can be controlled by the present invention.

Figure 9B:
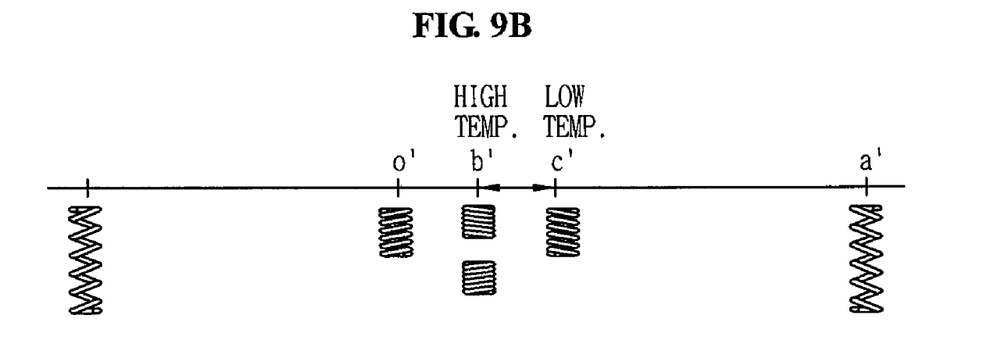

In the present invention, a wound direction of the coil spring was changed thus to obtain a coil showing a flexible memory effect by being completely closed when heated. As shown in FIG. 9B, a coil having an original shape (o') is prepared, and then is deformed by (a'). The coil is restored into (b') when heated, and is restored into (c') when cooled. The shape of the coil is changed into (b') and (c') by a heating process and a cooling process. Accordingly, a coil spring having a flexible shape memory effect and showing a completely closed state at a high temperature was prepared in the present invention. That is, in the conventional art, the coil spring was not able to be deformed more than the closed state. However, in the present invention, since the coil spring can be deformed more than the closed state by changing a wound direction thereof, the shape of the coil spring having a flexible shape memory effect can be freely controlled.

Figure 9C:
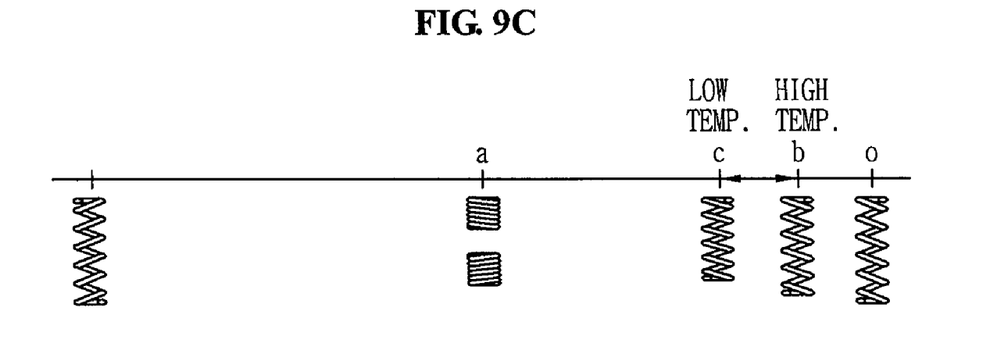

It is difficult to fabricate a coil spring completely contracted when cooled while expanded when heated. As shown in FIG. 9C, when the coil spring having an expanded shape (o) is compressed and then is heated, the shape of the coil spring becomes (b). The shape of the coil spring becomes (c) when cooled. Accordingly, the coil can maintain an expanded state even at a low temperature.

Figure 9D:
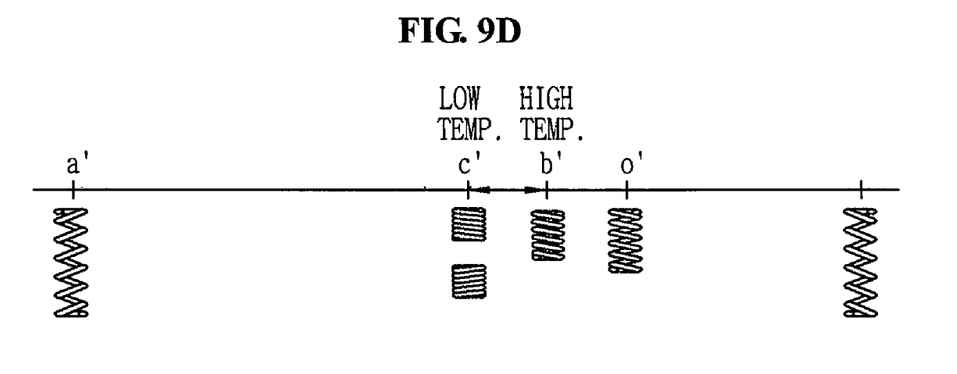

In the present invention, the conventional problem is solved by changing a wound direction of the coil spring. As shown in FIG. 9D, the original shape (o') of the coil spring is reversely changed and is deformed into (a'). The shape of the coil spring becomes (b') when heated, and becomes (c') when cooled. Accordingly, a coil spring completely closed when cooled and expanded when heated can be manufactured in the present invention.

Figure 9E:
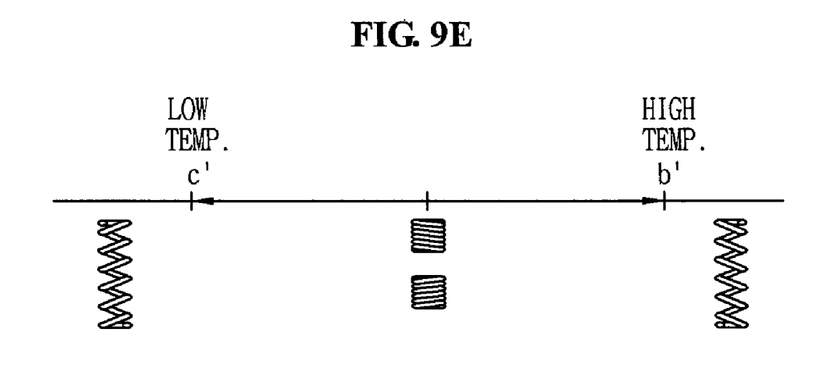

An operation direction of the coil spring according to the present invention can be changed. As shown in FIG. 9E, the coil spring showing a flexible shape memory effect can be expanded when heated, and can be expanded when cooled by reversely changing a wound direction thereof.

The coil spring according to the present invention has the following effects.

First, a large and precise initial tension can be provided to the coil spring.

Second, a moving distance of an actuator formed of a shape memory alloy (SMA) can be increased.

Third, the coil spring having been permanently deformed can be restored into the original state.

Fourth, the SMA coil spring can implement a flexible shape memory effect and a desired shape.

Fifth, an expanded and contracted direction of the coil spring can be changed according to a temperature.

It will also be apparent to those skilled in the art that various modifications and variations can be made in the present invention without departing from the spirit or scope of the invention. Thus, it is intended that the present invention cover modifications and variations of this invention provided they come within the scope of the appended claims and their equivalents.

The invention claimed is:

1. A method for providing an initial tension to a coil spring having a gap between each turn, comprising the steps of:
   shifting one end of the coil spring over an adjacent turn and into a first gap of the coil spring thereby generating a contact point between an inner side of an end turn and an outer side of the adjacent turn; and
   moving the contact point along an entire outer side of the coil spring by rotating the coil spring.

2. The method of claim 1, further comprising the step of inserting a supplementary device inside the coil spring prior to the step of shifting.

* * * * *